United States Patent [19]

Jansen

[11] Patent Number: 5,510,545
[45] Date of Patent: Apr. 23, 1996

[54] PROCESS FOR THE PREPARATION OF HYDROFLUOROCARBONS

[75] Inventor: Rolf-Michael Jansen, Kelkheim, Germany

[73] Assignee: Hoechst Aktiengesellschaft, Germany

[21] Appl. No.: 320,845

[22] Filed: Oct. 7, 1994

Related U.S. Application Data

[63] Continuation of Ser. No. 67,661, May 26, 1993, abandoned.

[30] Foreign Application Priority Data

May 26, 1992 [DE] Germany .................. 42 17 398.1

[51] Int. Cl.$^6$ ...................................... C07C 17/26
[52] U.S. Cl. ............................... 570/171; 570/176
[58] Field of Search ............................ 570/171, 176

[56] References Cited

U.S. PATENT DOCUMENTS

| | | | |
|---|---|---|---|
| 4,902,839 | 2/1990 | Bielefeldt et al. | |
| 4,954,666 | 9/1990 | Bielefeldt et al. | |
| 5,382,720 | 1/1995 | Ikawa et al. | 570/177 |
| 5,426,252 | 6/1995 | Sherif | 570/177 |

FOREIGN PATENT DOCUMENTS 9008753  8/1990  WIPO .................... 570/176

OTHER PUBLICATIONS

Haszeldine, R. N., *J. Chem. Soc.:* pp. 2504–2513 (1952).
Tomioka, S., et al, *Chemistry Letters:* pp. 1825–1826 (1991).

*Primary Examiner*—Alan Siegel
*Attorney, Agent, or Firm*—Connolly & Hutz

[57] ABSTRACT

The invention relates to a process for the preparation of saturated hydrofluorocarbons by hydrogenating at least one (hydro)fluorocarbon of the formula (I)

$$R_f\text{—}CH_nCl_cBr_dI_e \qquad (I)$$

in which
$R_f$ is $C_aF_{(2a-b)+1}H_b$ where a is 1–4 and b is 0–4,
n is 0–2
c is 0–3
d is 0–3
e is 0–3
c+d+e is 3–n,
catalytically with hydrogen at elevated temperature.

16 Claims, No Drawings

PROCESS FOR THE PREPARATION OF HYDROFLUOROCARBONS

This application is a continuation of application Ser. No. 08/067,661 filed May 26, 1993, now abandoned.

The present invention relates to the preparation of hydrofluorocarbons.

Hydrofluorocarbons are used as substitutes for the ozone-damaging fully halogenated chlorofluorocarbons (CFCs). Thus, for example, 1,1,1,4,4,4-hexafluorobutane (R 356) is a substitute for trichlorofluoromethane (R 11).

For this compound, specific preparation methods are already known. R 356 is formed, for example, on catalytic hydrogenation of 1,1,1,4,4,4-hexafluoro-2-butene (R. N. Hazeldine, J. Chem. Soc., 1952, page 2504). However, this starting material is toxic and can only be prepared uneconomically.

According to Tamioka et al., Chemistry Letters, page 1825–1826, 1991, Chemical Society of Japan, $F_3C$-$CCl_3$ (R 113a) can be converted in the presence of $H_2$ over Ni catalysts to 1,1,1,4,4,4-hexafluoro-2,3-dichloro-2-butene (R 1316). According to the details given in this publication, the R 113a does not give rise to any R 356. The very poisonous R 1316 preparable by this method can be used, according to DE-A-3,735,467 (which corresponds to U.S. Pat. No. 4,902,839 and U.S. Pat. No. 4,954,666) to prepare R 356 by catalytic hydrogenation in the presence of a base.

Surprisingly, it has now been found that R 113a can be converted directly into R 356 by catalytic hydrogenation and that similar starting materials can be analogously "reductively dimerized".

The invention provides a process for the preparation of saturated hydrofluorocarbons, which comprises hydrogenating at least one (hydro)fluorocarbon of the formula (I)

$$R_f\text{—}CH_nCl_cBr_dI_e \quad (I)$$

in which $R_f$ is $C_aF_{(2a-b)+1}H_b$ where a is 1–4 and b is 0–4, n is 0–2 c is 0–3 d is 0–3 e is 0–3 c+d+e is 3−n, catalytically with hydrogen at elevated temperature. c is preferably 1–3 and d and e are 0.

Examples of (hydro)fluorocarbons of the formula (I) which are suitable starting materials for the process according to the invention are 1-chloro-2,2,2-trifluoroethane (R 133a), 1,1-dichloro-2,2,2-trifluoroethane (R 123), 1,1,1-trichloro-2,2,2-trifluoroethane (R 113a) and 1,1-dichloro-2,2,3,3,3-pentafluoropropane. Preferably, 1,1,1-trichloro-2,2,2-trifluoroethane (R 113a) is used; in this case, R 356 is obtained in high yield and selectivity. However, it is also possible to use mixtures of two or more (hydro)fluorocarbons of the formula (I).

Suitable catalysts for the process according to the invention are elements from subgroups I to VIII of the Periodic Table, in particular elements from subgroup I, II or VIII. The elements can be present in the form of metals or in the form of compounds (for example as oxides or hydroxides) and in unsupported form or on support materials, such as activated carbon, $SiO_2$, $Al_2O_3$, MgO, $TiO_2$, $ZrO_2$. The catalysts are preferably used on support materials. Preferred support materials are activated carbon, $SiO_2$ and $Al_2O_3$.

The reaction temperature is in general 50° to 500° C., preferably 150° to 500° C. Preferably, one point of the reaction vessel is set to a minimum temperature $T_{min}$ and another point to a temperature $T_{max}$, which differ by at least 50 degrees. This $T_{min}$ is in general 50° to 450° C., preferably 150°–450° C., and $T_{max}$ is in general 100° to 500° C., preferably 200° to 500° C. The reactants are then preferably first exposed to the higher temperature $T_{max}$ and then to the lower temperature $T_{min}$. The same catalysts may be present at the point of maximum temperature and at the point of minimum temperature, in which case it is preferred to use Fe, Co, Cu or Ni, in particular Ni. Alternatively, two different catalysts can be used at the two points, in which case it is preferred to use Fe, Co, Cu or Ni, in particular Ni, at the point of maximum temperature and to use Ni, Ru, Rh, Pd or Pt, in particular Rh, at the point of minimum temperature.

It is also possible to establish in the reactor a high temperature zone A and a low temperature zone B, the temperature throughout zone A being at least 50° C. higher than in zone B. Preferably, the reactants first pass through zone A and then through zone B. The temperature within zone A can be constant, but it can also drop or rise from the beginning of the zone toward its end. The same is true of zone B. Preferably, the temperature in both zones drops from the beginning toward the end, in which case the temperature prevailing at the end of zone A is at least 50% higher than at the beginning of zone B through which the reactants pass afterwards. In the preferred embodiment of the process according to the invention, the reactants first pass through a zone A which is at 350°–550° C. and then through a zone B which is at 50°–300° C., in particular 150°–300° C.

The length of zones A and B is in general 10% to 50% each of the total length of the (elongate) reactor. This means that in the case of a tubular reactor 2 m in length each of the two zones has, for example, a length of 0.2 to 1 m.

In zone A and B, the same catalyst can be used, in which case it is preferred to use Fe, Co, Cu or Ni, in particular Ni. It is also possible, this being particularly preferred, to use two different catalysts in the two zones; in this case, it is preferred to use in zone A Fe, Co, Cu or Ni, in particular Ni, and to use in zone B Ni, Ru, Rh, Pd or Pt, in particular Rh.

The process according to the invention is in general carried out at pressures of 1 to 200 bar, preferably at 1 to 25 bar. The hydrogen/educt ratio is in general 1:1 to 20:1, preferably 4:1 to 10:1.

The examples which follow serve to illustrate the invention.

EXAMPLE 1

R 113a (50 ml/h; metered in liquid form by means of a diaphragm pump) and $H_2$ were passed through a reactor tube (L=2000 mm (ø=40 mm) packed with 500 g of an $Ni/SiO_2$ catalyst ($Ni/SiO_2$ ratio=1:5, for preparation, see Ueda et al., Chem. Letters, 1990, page 879–880), the hydrogen stream being set by a thermal mass flow controller to such a value that the molar $H_2$/R 113a ratio was 6:1. In the reactor tube, two different temperature zones each having a length of 800 mm were created by means of two independently controlled ovens. The temperature of the first zone (A) was 450° C., and that of the second zone (B) 220° C. The reaction gases formed were first passed through a water wash, then through a wash composed of 10% NaOH/water, and finally through a drying tower packed with molecular sieve and then condensed. The resulting products were identified by gas chromatography. The reaction mixture (30 g/h) had the following composition (in % by weight):

96.0% of 1,1,1,4,4,4-hexafluorobutane, 1.8% of 1,1,1-trichloro-2,2,2-trifluoroethane, 0.9% of 1-chloro-2,2,2-trifluoroethane, 0.5 % of 1,1,1-trifluoroethane, 0.3% of 1,1-dichloro-2,2,2-trifluoroethane, 0.3% of 2-chloro-1,1,1,4,4,4-hexafluoro-2-butene, 0.2% other.

EXAMPLE 2

The procedure of Example 1 was repeated, except that in the second reactor zone 0.8% Rh on activated carbon was used as the catalyst instead of the Ni/SiO$_2$ catalyst. The reaction mixture (30 g/h) had the following composition (in % by weight):

97.3% of 1,1,1,4,4,4-hexafluorobutane, 1.3% of 1,1,1-trichloro-2,2,2-trifluoroethane, 0.8% of 1-chloro- 2,2,2-trifluoroethane, 0.5% of 1,1,1-trifluoroethane, 0.1% of 1,1-dichloro-2,2,2-trifluoroethane, 0.1% of 2-chloro-1,1,1,4,4,4-hexafluoro-2-butene, 0.1% other.

What is claimed is:

1. A process for the hydrogenating dimerisation of at least one fluorocarbon or hydrofluorocarbon selected from the group consisting of 1-chloro-2,2,2-trifluoroethane, 1,1-dichloro-2,2,2-trifluoroethane, 1,1,1-trichloro-2,2,2-trifluoroethaneand 1,1-dichloro-2,2,3,3,3-pentafluoropropane, which comprises contacting said compound with hydrogen in the presence of at least one catalyst which contains an element from subgroups I to VIII of the Periodic Table, at an elevated temperature from 50° to 500° C.

2. The process as claimed in claim 1, wherein the catalyst used comprises Fe, Co, Cu or Ni.

3. The process as claimed in claim 1, wherein the catalyst used comprises Ni.

4. The process as claimed in claim 1, wherein the catalyst used at the point of maximum temperature comprises Fe, Co, Cu or Ni and the catalyst used at the point of minimum temperature comprises Ru, Rh, Pd or Pt.

5. The process as claimed in claim 1, wherein the catalyst used at the point of maximum temperature comprises Ni and the catalyst used at the point of minimum temperature comprises Rh.

6. The process as claimed in claim 1, wherein the reaction takes place in a reaction vessel and a zone A of the reaction vessel is set at a temperature of 350° to 500° C. and a zone B at a temperature of 150° to 300° C., and the reactants are passed first through zone A and then through zone B.

7. The process as claimed in claim 6, wherein the catalyst used in both zones comprises Fe, Co, Cu or Ni.

8. The process as claimed in claim 6, wherein the catalyst used in both zones comprises Ni.

9. The process as claimed in claim 6, wherein the catalyst used in zone A comprises Fe, Co, Cu or Ni and the catalyst used in zone B comprises Ru, Rh, Pd or Pt.

10. The process as claimed in claim 6, wherein the catalyst used in zone A comprises Ni and the catalyst used in zone B comprises Rh.

11. The process as claimed in claim 6, wherein the temperature in both zones drops from the beginning toward the end.

12. The process as claimed in claim 1, wherein the starting material used is 1,1,1-trichloro-2,2,2-trifluoroethane.

13. The process as claimed in claim 1, wherein said catalyst is used on support materials.

14. The process as claimed in claim 13, wherein said support materials are selected from the group consisting of activated carbon, SiO$_2$ and Al$_2$O$_3$.

15. The process as claimed in claim 14, wherein the reaction is carded out at pressure of 1 to 200 bar.

16. The process as claimed in claim 1, wherein the reaction is carded out at a pressure from 1 to 25 bar.

* * * * *